(12) United States Patent
Gu et al.

(10) Patent No.: US 12,082,947 B2
(45) Date of Patent: Sep. 10, 2024

(54) PHYSIOLOGICAL DETECTION DEVICE WITH WHITE LIGHT SOURCE

(71) Applicant: PIXART IMAGING INC., Hsin-Chu County (TW)

(72) Inventors: Ren-Hau Gu, Hsin-Chu County (TW); Chih-Hsin Lin, Hsin-Chu County (TW)

( * ) Notice: Subject to any disclaimer, the term of this patent is extended or adjusted under 35 U.S.C. 154(b) by 0 days.

(21) Appl. No.: 18/200,561

(22) Filed: May 22, 2023

(65) Prior Publication Data

US 2023/0309930 A1 Oct. 5, 2023

Related U.S. Application Data

(62) Division of application No. 17/523,609, filed on Nov. 10, 2021, now Pat. No. 11,717,228, which is a division of application No. 16/177,433, filed on Nov. 1, 2018, now Pat. No. 11,224,384.

(51) Int. Cl.
*A61B 5/00* (2006.01)
*A61B 5/024* (2006.01)
*A61B 5/0245* (2006.01)
*A61B 5/25* (2021.01)

(52) U.S. Cl.
CPC .......... *A61B 5/7207* (2013.01); *A61B 5/0006* (2013.01); *A61B 5/0064* (2013.01); *A61B 5/02416* (2013.01); *A61B 5/02405* (2013.01); *A61B 5/02438* (2013.01); *A61B 5/0245* (2013.01); *A61B 5/25* (2021.01); *A61M 2205/3303* (2013.01)

(58) Field of Classification Search
CPC ............ A61B 2562/066; A61B 5/0006; A61B 5/0064; A61B 5/02405; A61B 5/02416; A61B 5/02433; A61B 5/02438; A61B 5/0245; A61B 5/25; A61B 5/7207; A61B 5/7214; A61B 5/7264; A61M 2205/3303
See application file for complete search history.

(56) References Cited

U.S. PATENT DOCUMENTS 9,167,975 B1 * 10/2015 Brady .................... A61B 5/725
9,826,940 B1 * 11/2017 Lengerich .............. A61B 5/721

* cited by examiner

*Primary Examiner* — Michael T Rozanski
(74) *Attorney, Agent, or Firm* — Bruce Stone LLP; Joseph A. Bruce

(57) ABSTRACT

There is provided a physiological detection device including a white light source, a molding and a pixel array. The white light source is configured to emit white light having a color temperature between 2800K and 3200K. The molding is formed upon the white light source and configured to constrain an emission angle of the white light between 60 and 80 degrees. The pixel array is covered by a filter layer having a passband between 570 nm and 620 nm configured to filter the white light.

6 Claims, 4 Drawing Sheets

PHYSIOLOGICAL DETECTION DEVICE WITH WHITE LIGHT SOURCE

CROSS REFERENCE TO RELATED APPLICATION

The present application is a divisional application of U.S. Ser. No. 17/523,609, filed on Nov. 10, 2021, which is a divisional application of U.S. Ser. No. 16/177,433, filed on Nov. 1, 2018, the disclosures of which are hereby incorporated by reference herein in their entirety.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to the physiological detection and, more particularly, to a heart rate detection device capable of removing motion artifact caused by muscle activities by using light of multiple wavelengths and an operating method thereof.

2. Description of the Related Art

Conventionally, the heart rate detection can be performed by analyzing electrocardiogram (ECG). However, two electrodes are required to detect the ECG such that it is not convenient in operation. Therefore, in recent years an optical type of heart rate detection is used, and an optical heart rate detector is adaptable to portable and wearable electronic devices.

It is known that the optical physiological detection can be influenced by the relative movement between a detection device and a skin surface. Especially when an optical detection device is applied to a wearable device, a user likes to use the optical detection device to detect the heart rate variation during exercises such that the detection accuracy is degraded due to the influence of noises.

One conventional method to reduce the noises is to operate an optical physiological detection device in conjunction with an acceleration detector. The detection result of the acceleration detector is used to denoise the detection result of the optical physiological detection device so as to increase the detection accuracy. However, this kind of denoising method cannot remove noises caused by simple muscle activities, e.g., a user only moving his/her wrist or finger(s) without waving his/her arm. In this scenario, the acceleration detector is not able to generate usable results for denoising.

In addition, in the conventional physiological detection, the influence of noises on detection results caused by said simple muscle activities is not discussed, and the method of how to remove this motion artifact is not provided.

Accordingly, it is necessary to provide a physiological detection device capable of removing the motion artifact caused by muscle activities under a detected skin region so as to improve the detection accuracy.

SUMMARY

The present disclosure provides a heart rate detection device and an operating method thereof that perform a vector operation between a predetermined intensity distribution of multiple light colors and current light detection signals of the multiple light colors so as to eliminate the motion artifact in detected photoplethysmogram (PPG) signals.

The present disclosure further provides a physiological detection device with high detection efficiency and low power consumption.

The present disclosure further provides a physiological detection device including a white light source, a molding and a pixel array. The white light source is configured to emit white light having a color temperature between 2800K and 3200K. The molding is formed upon the white light source and configured to constrain an emission angle of the white light between 60 and 80 degrees. The pixel array is covered by a filter layer having a passband between 570 nm and 620 nm configured to filter the white light.

In the embodiments of the present disclosure, the light detector is used to sense reflected and scattered light from subcutaneous tissues illuminated by a light source of multiple wavelengths. The light source of multiple wavelengths is a white light emitting diode (LED) or white light laser diode (LD). Or, the light source of multiple wavelengths is formed by multiple LED dies or multiple LD dies respectively emitting light of different wavelengths. A distance between different dies is preferably smaller than 2000 micrometers such that emission lights therefrom go through substantially identical muscle fibers or bundles. For example, said different dies are formed on the same substrate.

In the embodiments of the present disclosure, it is preferably to use a single pixel matrix to operate in conjunction with a light source of multiple wavelengths. The pixel distance between pixels of said single pixel matrix is preferably smaller than 2000 micrometers to receive emergent lights from substantially identical muscle fibers or muscle bundles.

In the embodiments of the present disclosure, when the light source of multiple wavelengths is a white light source, a pixel array of the light detector is covered by a filter layer of multiple colors to achieve the purpose of detecting light of different colors. If the light source of multiple wavelengths is formed by multiple dies for emitting light of different colors, the pixel array of the light detector is not covered by a filter layer of different light colors. By lighting the dies to emit light of different colors at different times, the purpose of detecting light of different colors is also achievable.

In the embodiments of the present disclosure, at least two light wavelengths are used, and a wavelength difference between different light wavelengths is preferably larger than 25 nm to achieve a better denoising effect. However, if only two light wavelengths are used, the wavelength difference should be selected as large as possible, e.g., preferably larger than 50 nm.

BRIEF DESCRIPTION OF THE DRAWINGS

Other objects, advantages, and novel features of the present disclosure will become more apparent from the following detailed description when taken in conjunction with the accompanying drawings.

FIG. 1 is a schematic block diagram of a heart rate detection device according to one embodiment of the present disclosure.

DETAILED DESCRIPTION OF THE EMBODIMENT

It should be noted that, wherever possible, the same reference numbers will be used throughout the drawings to refer to the same or like parts.

The physiological detection device of the present disclosure is used to detect photoplethysmogram (PPG) signals, and calculate a heart rate and analyze the user state reflected by a heart rate waveform according to the PPG signals. In addition to eliminate noises caused by a relative movement between the device and a detected skin, the physiological detection device of the present disclosure further removes a motion artifact from muscle fibers or muscle bundles under the detected skin (even no relative movement between the device and the detected skin), e.g., caused by activities like typing, rotating wrist, folding fingers and stretching fingers.

Figure 1:
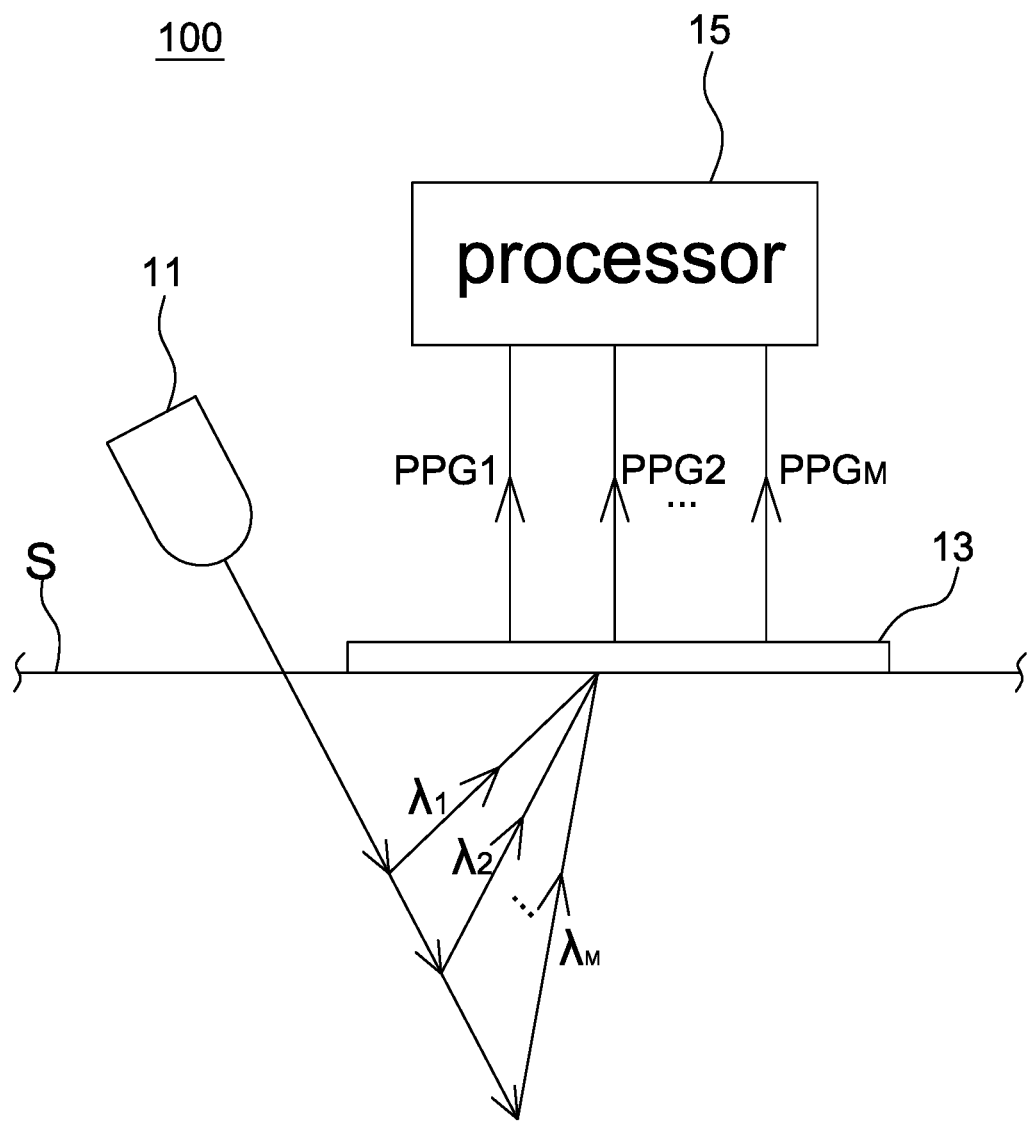

Referring to FIG. 1, it is a schematic block diagram of a heart rate detection device 100 according to one embodiment of the present disclosure. The heart rate detection device 100 includes at least one light source of multiple wavelengths 11, a light detector 13 and a processor 15, wherein the light detector 13 and the processor 15 are formed, for example, in the same sensor chip, but not limited to. In one non-limiting embodiment, the light source 11, the light detector 13 and the processor 15 are formed in one encapsulation, and embedded in a wearable or portable electronic device such as a watch or a cell phone.

The light source 11 includes, for example, a light emitting diode (LED), a laser diode (LD) or the like. The light detector 13 includes, for example, a CCD image sensor, a CMOS image sensor or the like. The processor 15 includes, for example, a digital signal processor (DSP), a microcontroller (MCU), a graphic processing unit (GPU), a central processing unit (CPU), an application specific integrated circuit (ASIC) or the like.

Each of the at least one light source 11 emits light covering or containing multiple wavelengths (e.g., $\lambda_1$, $\lambda_2 \ldots \lambda_M$ shown in FIG. 1) to illuminate a skin surface S of a user, wherein the skin surface S is determined according to an arranged location of the heart rate detection device 100, e.g., on a forearm or upper arm, without particular limitations. A wavelength range of the multiple wavelengths is determined according to a number of required wavelengths. For example, if a number of detection signals associated with different light colors required in calculating a heart rate (illustrated by an example below) is larger, a wider wavelength range is used. As shown in FIG. 1, although lights of different colors have different penetration depths, they still go through at least some identical tissues. For example, a wavelength difference between the different light colors is at least 25 nm to allow the detection signals to have enough difference therebetween.

The light detector 13 includes a sensing unit (e.g., a single pixel array 131 in FIG. 2A) used to output multiple light detection signals associated with different light colors corresponding to the multiple wavelengths, wherein the light detection signals are referred as PPG signals herein, e.g., FIG. 1 showing light detection signals $PPG_1$, $PPG_2 \ldots PPG_M$. As body tissues have different absorptivity on different light colors, different light detection signals have different intensities, e.g., referring to FIG. 3B.

Figure 2A:
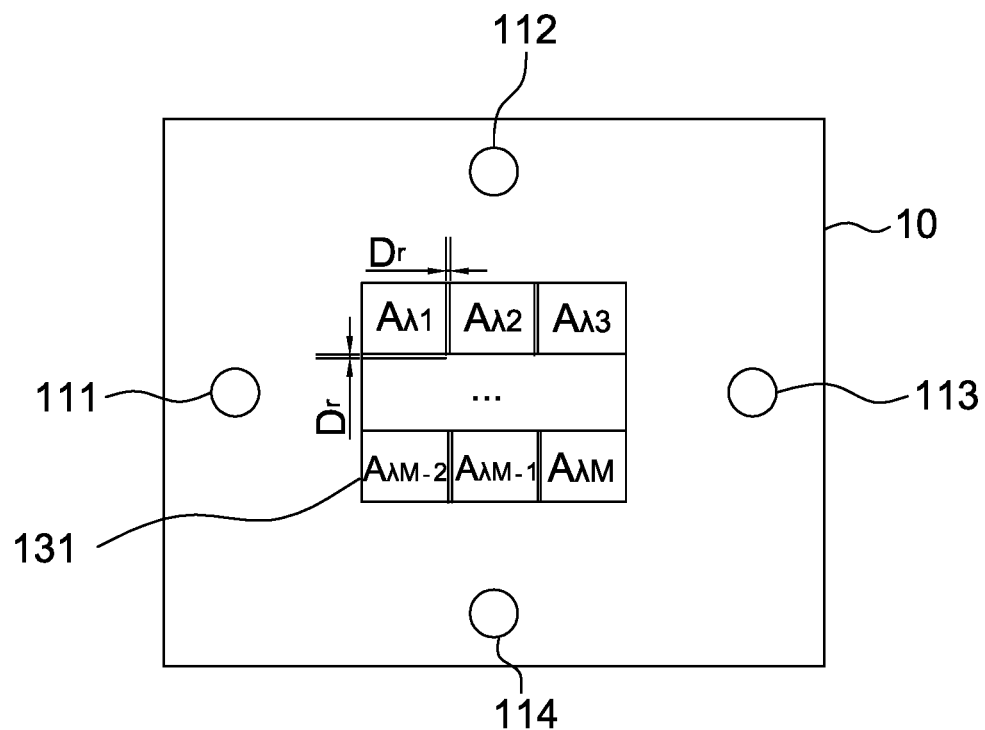
FIG. 2A is a schematic diagram of the arrangement of the light source and light detector of a heart rate detection device according to one embodiment of the present disclosure.
Figure 2B:
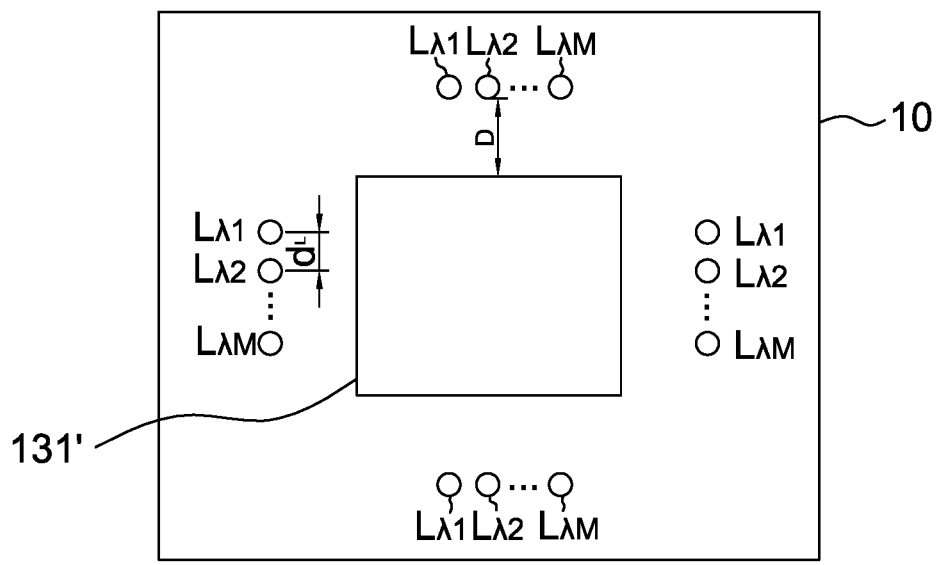
FIG. 2B is a schematic diagram of the arrangement of the light source and light detector of a heart rate detection device according to another embodiment of the present disclosure.

Referring to FIGS. 2A and 2B, they are schematic diagrams of arranging the light source and the light detector in a heart rate detection device according to some embodiments of the present disclosure.

In one non-limiting embodiment, the light source 11 is a white light source. The single pixel array 131 includes multiple pixel regions, e.g., FIG. 2A showing pixel regions $A_{\lambda 1}$ to $A_{\lambda M}$. The multiple pixel regions $A_{\lambda 1}$ to $A_{\lambda M}$ are covered by a filter layer of different light colors (e.g., corresponding to $\lambda_1$ to $\lambda_M$) to allow the multiple pixel regions $A_{\lambda 1}$ to $A_{\lambda M}$ of the single pixel array 131 to output multiple detection signals (e.g., $PPG_1$, $PPG_2 \ldots PPG_M$ shown in FIG. 1) associated with the different light colors. For example, the pixel region $A_{\lambda 1}$ outputs PPG1, the pixel region $A_{\lambda 2}$ outputs $PPG_2$, and so on.

Each pixel region $A_{\lambda 1}$ to $A_{\lambda M}$ includes one or multiple pixels. In one non-limiting aspect, each pixel region has a substantially identical area and further has a same number of pixels, but not limited thereto. When one pixel region includes multiple pixels, light detection signals of said multiple pixels are added by a hardware circuit or software codes to output a sum of light detection signals as the light detection signals $PPG_1$, $PPG_2 \ldots PPG_M$ shown in FIG. 1.

It should be mentioned that although FIG. 2A shows four white light sources 111-114 each emitting white light on a substrate 10, it is used to increase the possibility of detecting a motion artifact of muscles by the light detector 13. The heart rate detection device 100 of the present disclosure is for removing noises of tiny activities of muscles under the detected skin, and muscle bundles that have activities are determined according to the type of user's motion, such as finger movement. In some scenarios, emission light from light sources of multiple wavelengths 111 and 113 arranged at two opposite sides along a first direction of the pixel array 131 of the light detector 13 cause the pixel array 131 to detect a motion artifact but emission light from light sources of multiple wavelengths 112 and 114 arranged at two opposite sides along a second direction of the pixel array 131 of the light detector 13 do not cause the pixel array 131 to detect the motion artifact, or vice versa. Or emission light from all white light sources 111 to 114 can cause the pixel array 131 to detect the motion artifact.

More specifically, if tissues passed by emission light of one white light source have activities, the pixel array 131 can detect the motion artifact. Accordingly, employing only one white light source is sufficient, and it is not necessary to adopt multiple light sources each emitting light covering multiple wavelengths. It is also an option to arrange multiple white light sources surrounding the pixel array 131 to increase the detection possibility. In addition, as identical muscle fibers or muscle bundles are within a very small range, a distance Dr between two adjacent pixel regions $A_{\lambda 1}$ to $A_{\lambda M}$ is preferably smaller than 2000 micrometers, for example 1500, 1200, 1000, 800 or 600 micrometers, to effectively cancel the motion artifact. For example, when different pixel regions $A_{\lambda 1}$ to $A_{\lambda M}$ receive emergent light from different muscle fibers or bundles, the denoising function is degraded. Therefore, the region distance Dr is not simply a value of choice but with its physical meaning.

In another non-limiting embodiment, the pixel array 131' of the light detector 13 is not divided into multiple pixel regions for detecting different light colors as shown in FIG. 2B. The multiple light detection signals associated with different light colors are detected by controlling the light source of multiple wavelengths to emit light of different colors at different times. For example, the light source 11 includes a single die which is controlled to emit light of different wavelengths by controlling its driving parameter (e.g., driving voltage or current) or by controlling a variable color filter covering on the single die. Or, the light source 11 includes multiple dies (e.g., shown as $L_{\lambda 1}$ to $L_{\lambda M}$ in FIG. 2B) for emitting light containing or covering multiple wavelengths.

As mentioned above, to sense light from substantially identical muscle fibers or bundles, a die distance $d_L$ between the multiple dies $L_{\lambda 1}$ to $L_{\lambda M}$ in the light source 11 is preferably smaller than 2000 micrometers, e.g., the multiple dies being encapsulated within the same molding and on the same base layer, to allow the emission light therefrom to penetrate substantially identical muscle fibers or bundles to effectively cancel motion artifact caused by tiny activities. Similarly, the die distance $d_L$ is not simply a value of choice but with its physical meaning. Similarly, the multiple dies shown in FIG. 2B are selected to be arranged at a single side, two opposites sides or surrounding the pixel array 131'.

The processor 15 performs a vector calculation between multiple current light detection signals (e.g., obtained in a working mode) and a pre-stored intensity distribution or ratio of different light colors (e.g., obtained in a register mode) to cancel the motion artifact, wherein the pre-stored intensity distribution or ratio of the different light colors is obtained and stored by using the single pixel array 131 or 131' to detect multiple intensities of the multiple light detection signals $PPG_1$, $PPG_2$ ... $PPG_M$ associated with the different light colors when the user is motionless (i.e., muscles under the detected skin having no activity). That is, the heart rate detection device 100 further has a memory (including a volatile memory and/or a non-volatile memory) for storing the intensity distribution or ratio as well as the algorithm and parameters required for operation.

Figure 3A:
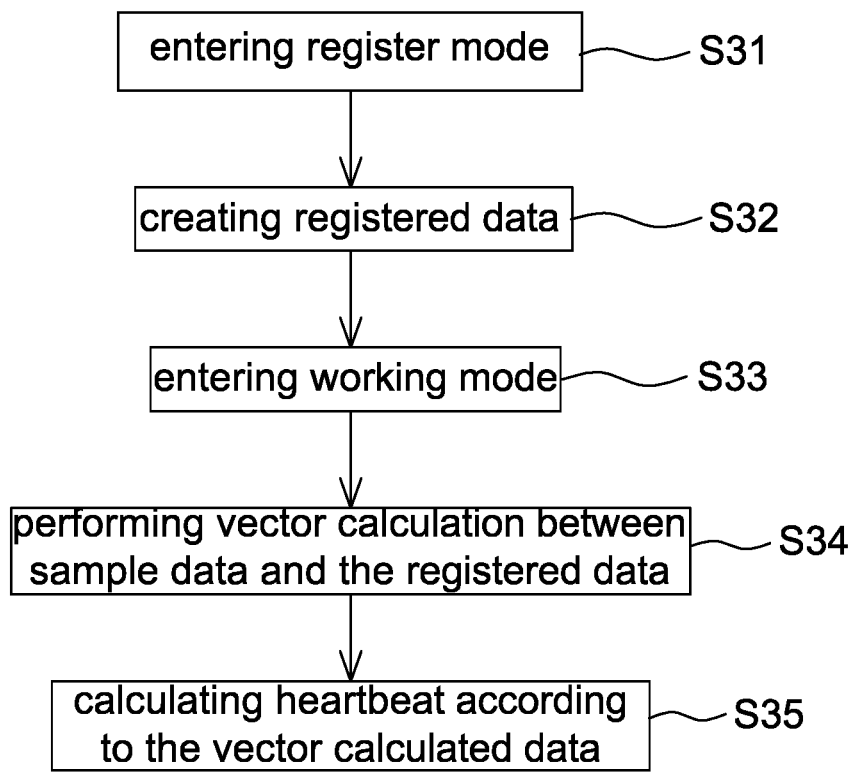
FIG. 3A is a flow chart of an operating method of a heart rate detection device according to one embodiment of the present disclosure.
Figure 3B:
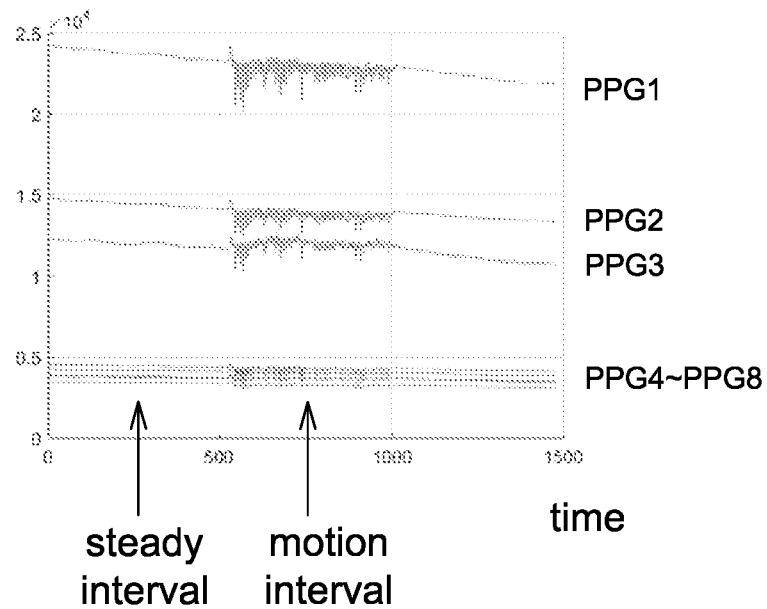
FIG. 3B is a schematic diagram of multiple light detection signals detected by a heart rate detection device according to one embodiment of the present disclosure.

Referring to FIGS. 3A and 3B, FIG. 3A is a flow chart of an operating method of a heart rate detection device according to one embodiment of the present disclosure which is applicable to the heart rate detection device 100 of FIGS. 1-3; and FIG. 3B is a schematic diagram of multiple light detection signals $PPG_1$, $PPG_2$ ... $PPG_M$ (i.e., corresponding to $\lambda_1$ to $\lambda_M$) detected by a heart rate detection device according to one embodiment of the present disclosure. The operating method of this embodiment includes the steps of: entering a register mode (Step S31); creating registered data in the register mode (Step S32); entering a working mode (Step 33); performing a vector calculation between sample data and the registered data in the working mode (Step S34); and calculating a heart rate according to the vector calculated data (Step S35).

As mentioned above, the register mode is a detection mode that a user is motionless, e.g., a steady interval in FIG. 3B. For example, when the user executes an APP or presses a button on a heart rate detection device 100, the heart rate detection device 100 enters the register mode. Meanwhile, the part of body of the user carrying the heart rate detection device 100 is completely steady so as to record registered data associated with different light colors. The registered data indicates the intensity distribution or ratio of light detection signals associated with different light colors when there is no motion artifact.

In the operating method of this embodiment, the working mode is referred to a mode that a user carries the heart rate detection device 100 in everyday life, e.g., a motion interval shown in FIG. 3B. The working mode is also entered when, for example, the user executes an APP or presses a button. If the light detection signals, which are detected in the working mode and contain the motion artifact, associated with different light colors are projected back to the pre-stored intensity distribution or ratio, the motion artifact can be removed.

Referring to FIGS. 1 and 3A-3B, details of FIG. 3A are described using an example below. The processor includes, for example, a normalizer, a filter and an intensity calculator.

Steps S31-S32: In the register mode, the processor 15 controls the light source 11 to illuminate a first skin surface of a user. Meanwhile, the pixel array 131 or 131' of the light detector 13 senses emergent light from the first skin surface to generate multiple first light detection signals associated with different light colors, e.g., $PPG_1$, $PPG_2$ ... $PPG_M$ shown in FIG. 3B, wherein the light detector 13 acquires a plurality of sections of sample data associated with different light colors (illustrated by an example below) at a fixed or adjustable sampling frequency. The processor 15 then uses the plurality of sections of sample data associated with different light colors to calculate and store registered data, which reflects the intensity distribution or ratio of light of different colors.

For example, the processor 15 continuously receives the multiple first light detection signals $PPG_1$, $PPG_2$ ... $PPG_M$ associated with different light colors. In the present disclosure, each light detection signal among the multiple light detection signals detected by the light detector 13 is referred to one channel, and each channel is associated with one of the multiple different light colors. The processor 15 samples, within each sampling interval, a predetermined number of sample points (e.g., L points herein) each at a different time of every channel of the multiple first light detection signals $PPG_1$, $PPG_2$ ... $PPG_M$ as one section of sample data. It is appreciated that a light wavelength range of one channel herein includes not only a single wavelength but multiple wavelengths within a predetermined light wavelength range, e.g., full width at half maximum (FWHM).

For example, the L sample points of all M channels within one sampling interval acquired by the processor 15 are indicated by an M×L matrix as one section of sample data. As time goes by, the processor 15 acquires one M×L matrix within every sampling interval, and thus the processor 15 acquires a plurality of sections of sample data from every channel of the multiple first light detection signals $PPG_1$, $PPG_2$ ... $PPG_M$ associated with different light colors within a register interval (i.e. one register interval including a plurality of sampling intervals) to obtain a plurality of M×L matrices.

Next, the normalizer of the processor 15 normalizes every section of sample data (i.e. each M×L matrix) of the plurality of sections of sample data (i.e. the plurality of M×L matrices) of the multiple first light detection signals. For example, the normalization is to remove the dc component from each sampled value.

After the normalization, the processor 15 selects to filter each section of the normalized sample data. For example, the filter of the processor 15 uses a digital filter having a passband between 0.5 Hz and 3.5 Hz to filter each section of the normalized sample values.

Then, the intensity calculator of the processor 15 calculates an average of a standard deviation of the plurality of sections of sample data (e.g., 20 sections of sample data being acquired per second, and thus 600 sections being acquired for seconds, but not limited to) of every channel within a register interval (a predetermined time interval, for example 30 seconds, but not limited to). Firstly, the processor 15 calculates a standard deviation of every section of sample data within the register interval. Then, the processor 15 calculates an average of the plurality of standard deviations of the plurality of sections of sample data of each channel.

Finally, the processor 15 obtains the intensity distribution of the calculated average values of every channel (e.g., PPG1-PPG8 herein), which is used as the registered data associated with different light colors.

The processor further includes a vector calculator operates in the working mode.

Steps S33-S34: In the working mode, the processor 15 controls the light source 11 to illuminate a second skin surface of the user, wherein the second skin surface is identical to or different from the first skin surface. Meanwhile, the pixel array 131 or 131' of the light detector 13 senses emergent light from the second skin surface to generate multiple second light detection signals associated with different light colors, e.g., $PPG_1$, $PPG_2$ ... $PPG_M$ as shown in FIG. 3B. It should be mentioned that methods of the pixel array 131 or 131' of the light detector 13 for acquiring the multiple first light detection signals and the second light detection signals are identical only they are acquired in different modes (or referred to different stages or different time intervals).

Similarly, the processor 15 samples, within each sampling interval, a predetermined number of sample points (e.g., L points herein) each at a different time of every channel of the multiple second light detection signals $PPG_1$, $PPG_2$ ... $PPG_M$ as one section of sample data. For example, the processor 15 also acquires one M×L matrix for each sampling interval, wherein the method of the processor 15 for acquiring the M×L matrix has been mentioned above, and thus details thereof are not repeated herein.

The normalizer of the processor 15 normalizes every section of sample data (i.e. every M×L matrix) of the multiple second light detection signals $PPG_1$, $PPG_2$ ... $PPG_M$, and then the filter of the processor 15 filters every section of the normalized sample data, wherein the normalizing and the filtering are identical to those mentioned above and thus details thereof are not repeated herein. It should be mentioned that the filters herein are used for improving the calculation accuracy, but the filters are not necessary to be implemented.

Figure 4:
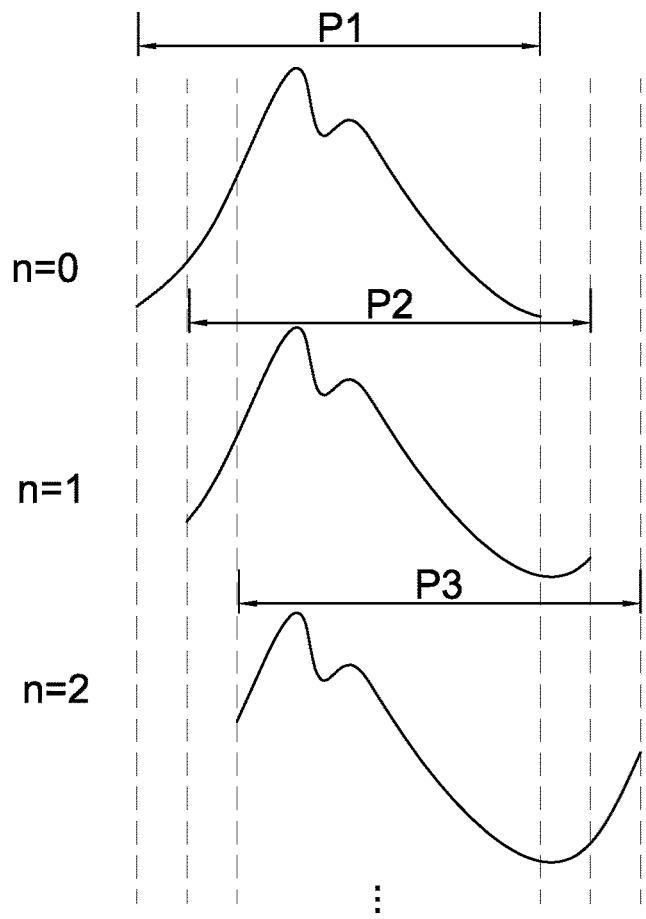
FIG. 4 is a schematic diagram of vector calculated data generated by a heart rate detection device according to one embodiment of the present disclosure.

Next, the vector calculator of the processor 15 performs a vector calculation between every section of sample data (i.e. $R_{M \times L}$) of the multiple second light detection signals and the registered data to cancel the motion artifact. For example, P is vector calculated data. In the working mode, the processor 15 outputs one set of heart rate data P, e.g., P1, P2, P3 ... as shown in FIG. 4, every one sampling interval, wherein the motion artifact no longer exists in the vector calculated data P. FIG. 4 shows the processor 15 outputs a plurality of vector calculated data P at continuous times (shown by n=0, 1, 2 ... ). A data number of each data set P is identical to a sampling number L within each sampling interval acquired by the processor 15.

In the present disclosure, the processor 15 samples a plurality of sections of sample data (i.e. a plurality of M×L matrices) in the register mode for creating the registered data, but samples one section of sample data (i.e. one M×L matrix) every sampling period in the working mode for the vector calculation with the registered data.

It is appreciated that channel numbers M of the multiple first detection signals and the multiple second detection signals are identical so as to perform the vector calculation. In one non-limiting embodiment, in the register mode the processor 15 uses more channels (e.g., 8 channels corresponding to 8 light colors 430 nm, 460 nm, 490 nm, 515 nm, 560 nm, 615 nm, 660 nm and 695 nm, but not limited to) to construct the registered data, and less channels are used in the working mode (e.g., 3 channels corresponding to 3 light colors 430 nm, 560 nm and 695 nm, but not limited to). The processor 15 only reads required data from the memory 17 during accessing the registered data. For example, in the working mode, when the detection result calculated by using one group of channels is not correct, e.g., noises still too high, another group of channels are used, by increasing, decreasing or maintaining the channel number. In other embodiments, channels among the multiple channels to be used are selected according to a ratio between the AC value and DC value of a PPG signal (referred as PI value herein), wherein a higher PI value indicates that a tissue response to the emission light is better. For example, a channel having a highest PI value is used in conjunction with the channel having a lowest PI value for the denoising process.

Finally, in the working mode, the processor 15 calculates a heart rate using the vector calculated data P in the time domain or frequency domain. For example, the processor 15 calculates the heart rate according to a time interval between two adjacent peaks or other corresponding kink points in the vector calculated data P, or the processor 15 converts the vector calculated data P into the frequency domain at first and then calculates the heart rate accordingly.

In one non-limiting embodiment, as the sampling frequency (or frame rate) of the light detector 13 is higher than the heart rate, to increase the signal intensity, the processor 15 further adds or overlaps a predetermined number of vector calculated data P or the vector calculated data P within a predetermined interval at first (e.g., P1+P2+P3+ ... in a section by section manner), and then calculates a heart rate according to a sum of or the overlapped vector calculated data P.

It should be mentioned that although the above operating method is illustrated in a way that multiple functional blocks are used to perform different functions, functions performed by every functional block are considered to be performed by the processor 15 using software codes and/or hardware codes.

As mentioned above, the registered data is the intensity distribution or ratio of light detection signals associated with every light color without the motion artifact (e.g., the steady interval shown in FIG. 3B). In actual operation if the user has some activities (e.g., the motion interval shown in FIG. 3B), the data intensity in the sampling matrix $R_{M \times L}$ of the second light detection signals is influenced by the noise to deviate from the pre-stored intensity distribution or ratio. The vector calculation of the present disclosure is to cause intensities of different light colors of the sampling matrix $R_{M \times L}$ to be projected to the pre-stored intensity distribution or ratio to remove the motion artifact.

In one non-limiting embodiment, the heart rate detection device of the present disclosure further includes a display (not shown) for showing the value and/or waveform of the heart rate.

It should be mentioned that the operating method of FIG. 3A mentioned above is only one embodiment applicable to the heart rate detection device 100, but not used to limit the present disclosure. The heart rate detection device 100 may use other algorithms to cancel noises as long as the light detector 13 detects emergent light from substantially identical muscle fibers or bundles, e.g., subtracting multiple light detection signals associated with different light colors from each other to remove the motion artifact.

It is appreciated that values mentioned in the above embodiments, such as light wavelengths, a number of light sources, a number of sampled points, a number of channels, are only intended to illustrate but not to limit the present disclosure.

A person skilled in the art would know that using white light has a poor efficiency, and thus a white light source is not applied to the physiological detection system. Meanwhile, according to the characteristics of luminescence materials, a monochromatic LED for emitting yellow light between 570 nm and 620 nm does not have high emission efficiency (i.e. consuming more power). Accordingly, although a PPG signal response (i.e. the above PI value) to light between 570 nm and 620 nm is better than to green light, the PI value is sacrificed and a green light source having better emission efficiency is selected to prevent using a yellow light source due to its high power consumption. To increase the PI value and reduce the power consumption (i.e. achieve high emission efficiency) at the same time, in one embodiment of the present disclosure, a white light source having a color temperature between 2800K and 3200K is used. Meanwhile, a filter layer having a pass band between 570 nm and 620 nm is covered on a pixel array of the light detector for filtering white light emitted by the white light source. In this way, the purposes of high PI value and low power consumption are achieved at the same time. For example, for detecting same PI values, using a white LED having a color temperature between 2800K and 3200K can have about three times of the emission efficiency than using the green LED or yellow LED. A significant improvement is achieved.

Figure 5:
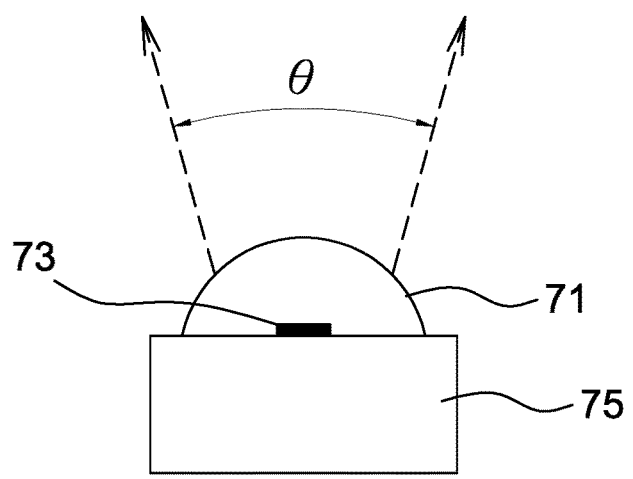
FIG. 5 is a schematic diagram of a white light source and a molding thereon of a physiological detection device according to one embodiment of the present disclosure.

In addition, an optical component is not used to constrain an emission angle of a white LED because the use purpose of the white LED is for space illumination such that a wide emission angle is required. Please referring to FIG. 5, to further improve the detection efficiency, a plastic or glass molding 71 is further formed on the white LED to cover a die 73 which is arranged on a base layer 75 of the white LED to constrain an emission angle θ of the white LED to be within 60 and 80 degrees to improve the system efficiency.

As mentioned above, the conventional physiological detection device can only cancel noises caused by stronger exercises but is not able to eliminate motion artifact caused by tiny muscle activities (e.g., those undetectable by an acceleration detector). Accordingly, the present disclosure further provides a heart rate detection device (e.g., FIGS. 1 and 2A-2B) and an operating method thereof (e.g., FIG. 3A) that use a single pixel array to detect reflected and scattered light from subcutaneous tissues illuminated by a light source, which emits light covering multiple wavelengths, to generate multiple light detection signals associated with different wavelengths. Based on an assumption that muscle activities have substantially identical influences on light detection signals of every light wavelength, the present disclosure cancel the motion artifact between light detection signals of different light wavelengths by, for example calculating the subtraction therebetween or vector projection, to obtain a clean heart rate waveform. This clear heart rate waveform can be used to calculate more correct heart rates.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A physiological detection device, comprising:
a white light source configured to emit white light having a color temperature between 2800K and 3200K;
a molding formed upon the white light source and configured to constrain an emission angle of the white light between 60 and 80 degrees; and
a pixel array covered by a filter layer having a passband between 570 nm and 620 nm configured to filter the white light.

2. The physiological detection device as claimed in claim 1, wherein the white light source comprising:
a base layer, on which the molding is formed; and
a die arranged on the base layer and covered by the molding.

3. The physiological detection device as claimed in claim 1, wherein the pixel array comprises multiple pixel regions each covered by a filter layer of different light colors to cause the multiple pixel regions of the pixel array to output multiple light detection signals associated with the different light colors.

4. The physiological detection device as claimed in claim 3, wherein a distance between the multiple pixel regions is smaller than 2000 micrometers.

5. The physiological detection device as claimed in claim 3, wherein a wavelength difference between the different light colors is 25 nm.

6. The physiological detection device as claimed in claim 1, wherein the molding is a glass molding or a plastic molding.

* * * * *